United States Patent [19]

Clark, Jr.

[11] Patent Number: 4,775,522

[45] Date of Patent: Oct. 4, 1988

[54] NMR COMPOSITIONS FOR INDIRECTLY DETECTING A DISSOLVED GAS IN AN ANIMAL

[75] Inventor: Leland C. Clark, Jr., Cincinnati, Ohio

[73] Assignee: Children's Hospital Research Foundation, a division of Children's Hospital Medical Center, Cincinnati, Ohio

[21] Appl. No.: 808,999

[22] Filed: Dec. 16, 1985

Related U.S. Application Data

[62] Division of Ser. No. 472,229, Mar. 4, 1983, Pat. No. 4,586,511.

[51] Int. Cl.$^4$ ............................................. A61K 49/00
[52] U.S. Cl. ......................................... 424/9; 128/653
[58] Field of Search ........................ 128/653; 324/309; 424/9

[56] References Cited

U.S. PATENT DOCUMENTS

| | | | |
|---|---|---|---|
| 4,297,637 | 10/1981 | Crooks et al. | 324/309 |
| 4,318,043 | 3/1982 | Crooks et al. | 324/309 |
| 4,319,190 | 3/1982 | Brown | 324/309 |
| 4,361,807 | 11/1982 | Burl et al. | 324/309 |

OTHER PUBLICATIONS

Harrison's Textbook of Medicine, p. I-124, McGraw Hill (10th Ed.), 1983.
Hamza, M. A. et al.: Solute-Solvent Interactions in Perfluorocarbon Solutions of Oxygen. An NMR Study, J. American Chemical Society, 103(13): 3733–3738 (1981).
Mansfield, P. et al, "NMR Imaging in Biomedicine", Academic Press, 1982, N.Y., N.Y., p. 230.
Gore, J. C. et al, "NMR Imaging at Hammersmith Hospital", SPIE, vol. 273, Application of Optical Instr. in Medicine IX, 1981.
Hamza, M. A. et al: Fluorocarbons as Oxygen Carriers. II, An NMR Study of Partially or Totally Fluorinated Alkanes and Alkenes, J. Magnetic Resonance, 42:227–241 (1981).
Hall, L. D. and Sukuman, S.: Chemical Microscopy Using a High-Resolution NMR Spectrometer. A Combination of Tomography/Spectrosopy Using Either $^1$H or $^{13}$C., 50:161–164 (1982).
Lauterbur et al: Zeugmatographic High Resolution Nuclear Magnetic Resonance Spectroscopy Images of Chemical Inhomogeneity Within Macoscopic Objects. J. American Chemical Society, 97(23):6866–6868, Nov. 12, 1975.
Holland, G. N. et al: $^{19}$F., Magnetic Resonance Imaging. J. Magnetic Resonance, 28:133–136 (1977).
Thomas, S. R. et al: Nuclear Magnetic Resonance Imaging Techniques as Developed Modestly Within a University Medical Center Environment: What Can the Small System Contribute at this Point", Magnetic Resonance Imaging. 1(1):11–21 (1981).
Delpuech, J. J., Hamza, M. A. and Serratrice, G.: Determination of Oxygen by a Nuclear Magnetic Resonance Method, J. Magnetic Resonance, 36:173–179 (1979).
Gadian, D. G.: Nuclear Magnetic Resonance and its Applications to Living Systems. 1st ed., Oxford: Clarendon Press, pp. 23–42 (1982).
Moon, R. B. and Richards, J. H.: Determination of Intracellular pH by $^{31}$P Magnetic Resonance. J. Biological Chemistry, 218(20):7276–7278 (Oct. 25, 1973).
Kramer, D. M.: Imaging of Elements Other Than Hydrogen. In Kaufman, L., Crooks, L. E. and Margulis, A. R.: Nuclear Magnetic Resonance Imaging in Medicine. 1st ed., New York-Tokyo: Igaku-Shoin Ltd., pp. 184–203 (1981).

*Primary Examiner*—Francis J. Jaworski
*Attorney, Agent, or Firm*—Wood, Herron & Evans

[57] ABSTRACT

A novel and improved method to detect and/or measure indirectly at least one gas, particularly dissolved gases, of an animal employing nuclear magnetic resonance techniques (NMR). The method examines an NMR spectrum to determine chemical shift relaxation times or spin-spin couplings for an element of an animal influenced by at least one gas of the animal. Uniquely, the gas detected according to the principles of this invention may be insensitive to present NMR techniques. Further, the present invention discloses a novel method to determine and monitor gaseous physiological states of an animal. Because of the unique and advantageous non-invasive, non-destructive and non-ionizing properties, the present invention may be employed in an animal continuously and in vivo. Still further, the present invention provides for the imaging of at least one-, two-, or three-dimensional projections reconstructed from a chemical shift, relaxation times, or spin-spin couplings for an element of an animal influenced by at least one gas in the animal. Novel compounds directed to providing radio-frequency reference signals in which chemical shifts may be determined therefrom are also disclosed.

11 Claims, No Drawings

NMR COMPOSITIONS FOR INDIRECTLY DETECTING A DISSOLVED GAS IN AN ANIMAL

This is a division, of application Ser. No. 472,229, filed Mar. 4, 1983, and now U.S. Pat. No. 4,586,511.

BACKGROUND OF THE INVENTION

Nuclear magnetic resonance, hereinafter NMR, is relatively a recent method in radiology with respect to the study and imaging of intact biological systems. Like X-rays and ultrasound procedures, NMR is a non-invasive analytical technique employed as a means to examine a body. Unlike X-rays, however, NMR is a non-ionizing, non-destructive process that can be employed continuously to a host. Further, NMR imaging is capable of providing anatomical information comparable to that supplied by X-ray "CAT" scans. In comparison to ultrasound, the quality of projections (images) reconstructed from currently known NMR techniques either rival or transcend those observed with ultrasound procedures. Thus, these rather unusual and highly desirable characteristics provide NMR with present potential to be one of the most versatile and useful diagnostic tools ever used in biological and medical communities.

Basically, NMR is a process that results when nuclei with magnetic moments are subjected to a magnetic field. If electromagnetic radiation in the radio-frequency of the spectrum is subsequently applied, the magnetized nuclei will emit a detectable signal having a frequency similar to the one applied.

More specifically, NMR predicates on the fact that nuclei with an odd number of nucleons have an intrinsic magnetism resulting from an angular momentum, or spin, of such nuclei. Resembling a bar magnet, the spin property generates a magnetic dipole, or magnetic moment, around such nuclei. Thus, when two external fields are applied to an object, the strong magnetic field causes the dipoles for such nuclei, e.g., nuclei with spin designated ½, to align either parallel or anti-parallel with said magnetic field. Of the two orientations, the parallel alignment requires the nuclei to store less energy and hence is the stable or preferred orientation. As to the second applied field, comprising radio-frequency waves carrying a precise frequency or quantum of electromagnetic radiation, it will cause such nuclei to nutate or flip into the less stable orientation. In an attempt to re-establish the preferred parallel or stable orientation, the excited nuclei will emit the absorbed electromagnetic radio waves at a frequency characteristic to the nuclei being detected.

Thus, the NMR technique detects radio-frequency signals emitted from nuclei with an odd number of nucleons as a result of a process undergone by such nuclei when exposed to at least two externally applied fields. If a third magnetic field in the form of a gradient is applied, nuclei with the same magnetogyric constant will nutate at different frequencies, i.e., Larmor frequencies, depending upon the location within the object. Thus, similar nuclei in an object can be detected discriminately for a particular region in said object according to their Larmor frequency corresponding to a particular magnetic field strength along the applied magnetic gradient, as demonstrated by the following equation $f_o = (\gamma) H_o$ wherein $f_o$ is the Larmor frequency, $\gamma$ is the magnetogyric constant, and $H_o$ is the applied magnetic field.

Unfortunately, there are several factors that may limit the usefulness of NMR applications in vivo. In general, NMR is an insensitive radiologic modality requiring significant amounts of nuclei with magnetic moments, i.e., an odd number of nucleons, to be present in an object. Consequently, not all nuclei in vivo are present in sufficient quantities to be detected by present NMR techniques. Further, not all nuclei in vivo have magnetic moments, i.e., an odd number of nucleons. Some of the more common isotopes that do not have magnetic moments which are found in vivo include carbon-12, oxygen-16, and sulfur-32. Thus, current NMR applications in vivo are restricted to those nuclei that have magnetic moments and are sufficiently abundant to overcome the insensitivity of present NMR techniques.

Heretofore, NMR applications in vivo have almost invariably been concerned with imaging or detecting the water distribution within a region of interest derived from the detection of proton resonance. Other nuclei not only have lower intrinsic NMR sensitivities, but also are less abundant in biological material. Consideration has, however, been given to the use of other nuclei such as phosphorous-31 which represents the next best choice for NMR in vivo applications due to its natural and abundant occurrence in biological fluids. For example, phosphorous-31 NMR has been found to provide a useful means for determining indirectly intracellular pH and $Mg^{++}$ concentration simply by measuring the chemical shift of the inorganic phosphate resonance in vivo and determining from a standard titration curve the pH or $Mg^{++}$ concentration to which the chemical shift corresponds. The type of information available from NMR. IN: Gadian, D. G.: *Nuclear Magnetic Resonance and Its Applications to Living Systems*. First Edition. Oxford: Clarendon Press. pp. 23–42 (1982); Moon, R. B. and Richards, J. H.: Determination of Intracellular pH By $^{31}P$ Magnetic Resonance. *J. Biological Chemistry*. 218(20):7276–7278 (Oct. 25, 1973). In addition, sodium-23 has been used to image an isolated perfused heart with a medium containing 145 mM sodium in vivo. Unfortunately, difficulties with these nuclei arise because of the inherent sensitivity losses due to the lower resonant frequencies of these nuclei. Moon, R. B. and Richards, J. H.: Determination of Intracellular pH By $^{31}P$ Magnetic Resonance. *J. Biological Chemistry*. 218(20):7276–7278 (Oct. 25, 1973).

Another stable element which is uniquely suited for NMR imaging is fluorine because its intrinsic sensitivity practically is commensurate with that of protons, it has a spin of ½, so as to give relatively uncomplicated, well-resolved spectra, its natural isotopic abundance is 100 percent, it gives large chemical shifts, and because its magnetogyric constant is similar to that of protons, the same equipment can be used. Unfortunately, fluorine NMR applications in vivo are in effect not conducted due to the practical non-existence of fluorine in biological materials. However, nuclear medicine procedures using the positron emitter fluorine-18 are well documented and include, for example, bone scanning, brain metabolism and infarc investigations using fluorodeoxyglucose, and myocardial blood flow and metabolism. With respect to fluorine NMR imaging, some investigations into such applications have been made. Suggestions have been presented involving the study of vascular system disorders, in conjunction with fluorocarbon blood substitutes, Holland, G. N. et al: $^{19}F$. Magnetic Resonance Imaging. *J. Magnetic Resonance*. 28:133–136

(1977), and the localization/kinetics of fluorocarbon following liquid breathing. Further, in vitro canine studies involving the investigation of the feasibility of fluorine as an agent for NMR imaging of myocardial infarction have also been performed. Thomas, S. R. et al: Nuclear Magnetic Resonance Imaging Techniques has developed Modestly Within a University Medical Center Environment: What Can the Small System Contribute at this Point? *Magnetic Resonance Imaging.* 1(1):11–21 (1981). Further, an NMR technique in an object other than an animal has been described for the determination of magnetic susceptibilities of oxygen in benzene or hexafluorobenzene solutions in order to estimate the amount of dissolved oxygen therein. For example, this method might be used for a remote control of oxygen content in organic solvents for oxygen pressures higher than one atmosphere. Delpuech, J. J., Hanza, M. A., and Serratrice, G.: Determination of Oxygen By a Nuclear Magnetic Resonance Method. *J. Magnetic Resonance.* 36:173–179 (1979). Finally, it has been demonstrated with NMR techniques in an object other than an animal that the solubilities of oxygen (in mole fractions) are higher in fluoroalkanes than in previously reported hexafluorobenzene. Hanza, M. A. et al: Fluorocarbons as Oxygen Carriers. II. An NMR Study of Partially or Totally Fluorinated Alkanes and Alkenes. *J. Magnetic Resonance.* 42:227–241 (1981).

As to biological gases, it is well known that in vivo gases are indicators with respect to diagnosing and monitoring physiological conditions in a host. Thus, it is critical to measure the gases with an accurate, inexpensive and reliable procedure. Heretofore, the biological gases measured in a host are practically limited to blood gases, and in particular, oxygen and carbon dioxide. Basically, the presently utilized procedures to measure blood gases include electrochemical, non-electrochemical, transcutaneous and infrared procedures. The electrochemical procedure is an analytical method designed to measure blood gases very accurately, inexpensively and quickly. In contrast, the non-electrochemical procedure, or the Van Slyke procedure is very slow, expensive and cumbersome. Unfortunately, both blood procedures are invasive requiring venipuncture or vascular intrusion. With respect to the transcutaneous procedure, this method is a continuous process capable of monitoring blood gases in a host over a period of time. The procedure requires the use of a Clark oxygen electrode probe to measure the blood gases. Finally, the infrared method, or the Jobsis procedure, measures the percent saturation of oxygen in the blood. However, this procedure requires subjecting the host to infrared rays.

It is apparent from the above brief overview directed to the limitation of NMR techniques and various methods for measuring in vivo gases and the current state of knowledge, that there is a need to provide improved methods that more effectively, measure, identify and monitor gases in an animal.

SUMMARY OF THE INVENTION

The present invention is directed to a novel method of detecting at least one gas particularly dissolved gases non-invasively of an animal utilizing nuclear magnetic resonance (NMR) techniques. Essentially, the novel method involves detecting indirectly at least one gas of an animal by observing chemical shifts derived from an element influenced by at least one gas. Thus, gases of an animal that presently are insensitive to NMR techniques may now be detected in accordance with the principles of the present invention. One main advantage of the invention is that in vivo gases may be detected non-invasively, non-destructively, accurately and continuously by NMR techniques. Another advantage is that homogeneous gases such as biological oxygen or a foreign anesthetic may be detected, as well as any mixture of gases.

It has been an objective of this invention, therefore, to provide a novel method of detecting at least one gas of an animal comprising subjecting an animal containing at least one gas to an NMR spectrometer to detect a radio-frequency signal derived from an element of the animal influenced by said gas, detecting another radio-frequency signal derived from an element independent of the animal and uninfluenced by the gas, and comparing the detected signals to detect at least one said gas. The difference between the detected signals, or chemical shift, corresponds to the amount and identity of at least one gas of the animal. In furtherance of the novel method, two or more radio-frequency signals derived from an element of an animal influenced by a gas may be detected to detect a gas of an animal without departing from the scope or principles of the present invention. Once chemical shifts have been observed for an element influenced by at least one gas of animal, such chemical shifts may be compared to standard NMR chemical shifts determined and established for an element in the presence of varying amounts of known gases as a means to determine the amount and identity of at least one said gas in the animal.

In accordance with the present invention, the element detected is, but not limited to, fluorine. When the element being detected is fluorine, a perfluorocarbon compound or composition may be introduced into the animal as a means to provide in an animal sufficient detectable amounts of fluorine. An example of such a perfluorocarbon is perfluorodecalin. Aqueous artificial blood compositions containing such a suitable perfluorocarbon compound may be used.

Accordingly, the present invention is predicated in part upon the observed chemical shifts which may further be processed to reconstruct at least one projection of at least one gas of an animal when spatial resolution is of interest. Further, the projection may be reconstructed into one-, two- or three-dimensional images. Thus, the present invention provides a non-invasive, non-destructive method to generate a one-, two-or three-dimensional gaseous map of an animal in vivo.

In practicing the present invention, the novel method may be utilized to determine and monitor continuously gaseous physiological states of an animal in vivo.

In another embodiment of the present invention, when a perfluorocarbon molecule having at least one proton in its structure, is introduced into an animal, said proton may provide a radio-frequency reference signal for fluorine as a means to determine chemical shift for the detected fluorine influenced by at least one gas in an animal. In the alternative to the proton, deuteron may be employed to provide such a reference point. Further, a proton or deuteron reference signal may be derived from water or $D_2O$, respectively, either within a biological fluid or a perfluorocarbon emulsion. Still further, the reference signal may be derived from an element or moiety of a perfluorocarbon which is positioned in the internal phase of the emulsion.

It is acknowledged by the inventor herein that U.S. Pat. Nos. 4,319,190 and 4,361,807 disclose methods of imaging chemical shifts in a body. However, even though such methods to image chemical shifts were reported, it had not been previously known that such methods may be uniquely effective to image indirectly gases within an animal that presently are insensitive to NMR techniques. Furthermore, such findings and other advantages of the present invention and the manner of their implementation as described herein are considered unexpected and unobvious and will become more apparent upon the following detailed description.

DETAILED DESCRIPTION OF THE INVENTION

In a presently preferred embodiment, practice of the novel method of this invention to detect at least one gas particularly dissolved gases of an animal employs examination of an NMR spectrum for a detected element of an animal influenced by said gas and an NMR spectrum for a detected element independent of an animal uninfluenced by said gas. Such examination provides for the determination of a gas of an animal from chemical shifts, relaxation times, i.e., $T_1$ or $T_2$, and spin-spin couplings derived from at least one radio-frequency signal for an animal influenced by at least one said gas as a means to detect indirectly said gas. The gases being detected according to the principles of this invention, however, need not be sensitive to NMR techniques. Further, a gas detected may be a paramagnetic gas. Thus, the novel method of the present invention detects indirectly at least one insensitive gas of an animal by its affects on the spectrum, i.e., chemical shift, of a detectable element. By chemical shift, as defined in the Glossary IN: Kaufman, L., Crooks, L. E. and Margulis, A. R.: *Nuclear Magnetic Resonance Imaging in Medicine*, First Edition. New York-Tokyo: Igaku-Shoin. p. 233 (1981), it refers to the shielding effect that electronic orbital motions have on the magnetic field at a nucleus. The chemical shift will therefore be proportional to the applied magnetic field and may be observed as displaced peaks on a spectrum. Chemical shift can further be defined as the difference between the strength of an external magnetic field and the resulting field at a selected element being detected. This result is produced by the local environment surrounding the element. Therefore, it is to be understood according to the principles of the present invention, that since the shielding influence of a gas in an animal will characterize the gas, chemical shift will correspond to an amount and identity of the gas in an animal.

Accordingly, the broadest aspect of my invention is to provide a novel and improved method of detecting indirectly at least one gas of an animal utilizing NMR techniques. More specifically, the method involves the obtainment of an NMR spectrum to determine chemical shift, relaxation times or spin-spin couplings for a detected element of an animal influenced by at least one gas in said animal to detect said gas. In another broad embodiment, this invention may detect gases that previously were undetectable by present NMR techniques. In still another broad embodiment, the invention may image at least one gas in an animal as a means to determine and monitor gaseous physiological states, reactions or biological processes of said animal. The inventive method is unique because it is non-invasive, non-destructive and non-ionizing to an animal. Further, it may be employed continuously to obtain the above mentioned determinations or results.

The novel method of detecting at least one gas of an animal according to the principles of my invention comprises subjecting said animal to an NMR spectrometer, detecting a first radio-frequency signal derived from resonance of an element of said animal influenced by said gas, detecting a second radio-frequency signal derived from an element independent of said animal uninfluenced by said gas, and comparing said signals to detect at least one said gas. Further, two or more radio-frequency signals may be detected that are derived from an element of an animal as a means to detect a gas. The difference between the detected signals corresponds to chemical shift, i.e., the shielding influence of said gas, for a detected element. In other words, the detected spectrum of radio-frequency signals is a measure of emitted wave energy attributable to the relaxation of the detected nuclei from its excited state to its stable state. Therefore, the chemical shift may be interpreted to correspond to an amount and identity of at least one gas in the animal.

Different spectra are obtained for such emitted radio waves by such nuclei in the presence of a gas as contrasted with the absence of the same gas. Thus, the differing spectrum provide a means of detection or measurement of the gas which is influencing the spectrum of the detectable nuclei. The determination of chemical shift provides the parameter representative of an amount and identity of said gas. For instance, the determined chemical shift may be compared to standard chemical shifts determined and established for an element influenced by variable amounts of the gas independent of an animal as a means to determine the amount and identity of the gas. It should be indicated, however, that signals detected for elements independent of an animal will preferably be in an environment similar to that in the animal but without the influence of the gas. Unless, of course, standard chemical shifts are determined and established for elements influenced by known quantities of identified gases.

Further, a gas may be detected from additional parameters such as relaxation times and spin-spin couplings derived from the radio-frequency signals of the detected elements. The relaxation times consists of $T_1$ or $T_2$ wherein $T_1$, spin-lattice relaxation time, constitutes the time it takes for the stimulated nuclei to re-establish stability and $T_2$, spin-spin relaxation time, is a measure of the time uniformity for the stimulated nuclei is lost. Of course, gaseous maps in an animal in vivo may be obtained in one-, two-, or three-dimensional images from either $T_1$ or $T_2$ derived from for example inversion recovery from $T_1$ or spin-echo from $T_2$. Spin-spin coupling corresponds to the perturbations in the detected signal as a result of surrounding magnetized nuclei which corresponds to a gas. Such a parameter may also be used to detect and image a gas in an animal.

In another aspect of the present invention, the two detected signals may be derived from the same or different elements, and preferably from the same element. This is not to say that when the signals are detected from unlike elements the method will be less effective in detecting a gas in an animal. But rather, a further step will be required to calibrate the difference in effect when unlike elements are detected.

In another aspect in accordance with the present invention, the presently preferred element to detect in an animal as a means to indirectly detect at least one gas is fluorine. As stated in the background, fluorine is uniquely suited for NMR techniques because it has a spin ½, giving relatively uncomplicated and well-resolved narrow spectral lines, 100 percent natural isotopic abundance, large chemical shifts, a magnetogyric constant similar to protons so that the same equipment may be used and relatively low natural biological occurrence. In order to follow the teachings of this invention, one must introduce into an animal a compound containing a sufficient amount of fluorine so that fluorine may be detected by NMR techniques. By introduce, it refers to the administration of a compound by inhalation, injection, oral introduction or other appropriate means. Further, such fluorine compounds must be chemically compatible with the animal, physically compatible for formulation of a composition that may be suitably introduced into an animal, and provide unambiguous, easily discernible NMR signals so that chemical shift can be accurately determined. It has been found that perfluorocarbons and any derivatives thereof are ideally suited for application according to the principles of the present invention. It is well known that such compounds dissolve large quantities of gases, e.g., oxygen, carbon dioxide, nitrogen, etc., and can be formulated so that they are chemically and physically compatible. Further, the shielding effects by gases can be easily observed with these compounds due to their high affinity for gases. Still further, these compounds are relatively incompatible with their surrounding environments and, thus, will provide chemical shifts that correspond reliably to the influence of the gases. Another advantage to these compounds is that they should provide unambiguous, easily discernible signals enabling chemical shifts due to shielding influences of at least one gas in an animal to be readily determined. The preferred perfluorocarbons or any derivatives thereof that may be used according to the teachings of this invention are perfluorocyclocarbons or emulsions thereof such as those employed in artificial bloods. Nevertheless, any perfluorocarbon or derivative thereof may be used in this present invention that demonstrates RES-phobic properties as is defined in my U.S. Pat. Nos. 3,911,138 and 4,105,798. Such fluorinated compounds may be mono or polyfluorocompounds, for instance, monofluoroacetylsalicyclic acid. Further, such fluorinated compounds may be substituted with or incorporated in their structure other atoms including metals such as iron. Further, other such fluorinated compounds include perfluoro(methylcyclohexane), perfluoro-1-methyldecalin [also known as perfluoro(decahydro-a-methylnaphthalene)], perfluoro (1,3-dimethylcyclohexane), perfluoro (decahydronaphthalene), and perfluoro (decahydrodimethylnaphthalene), or mixtures thereof, perfluorinated bicyclononane, perfluorinated bicyclooctane, perfluorinated adamantane hydrocarbon, perfluoromethyladamantane and perfluorodimethylbicyclo[3.3.1.]nonane, perfluorodimethyladamantane and perfluorotrimethylbicyclo[3.3.1.]nonane, perfluorotetrahydrodicyclopentadiene, perfluorinated bicyclononane, perfluorinated bicyclooctane, perfluorinated adamantane hydrocarbon, perfluoromethyladamantane and perfluorodimethylbicyclo[3.3.1]nonane, perfluorodimethyladamantane and perfluorotrimethylbicyclo[3.3.1.]nonane, and perfluorotetrahydrodicyclopentadiene and perfluorobicyclo[5.3.1]decane, and perfluorotributylamine (FC47) perfluorodecalin (PP5), perfluorotetrahydrofuran (FC80), perfluoroether (PID) [(CF$_3$)$_2$CFOCF$_2$(CF$_2$)$_2$CF$_2$OCF(CF$_3$)$_2$], perfluoroether (PIID) [(CF$_3$)$_2$CFOCF$_2$(CF$_2$)$_6$CF$_2$OCF(CF$_3$)$_2$],

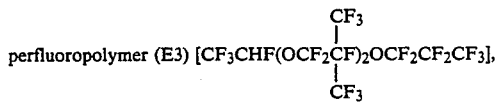

perfluoropolymer (E3) [CF$_3$CHF(OCF$_2$CF)$_2$OCF$_2$CF$_2$CF$_3$], perfluoropolymer (E4) [CF$_3$CHF(OCF$_2$CF)$_3$OCF$_2$CF$_2$CF$_3$], perfluoroetherpolyer (Fomblin Y/01), perfluorododecane, perfluorobicyclo[4.3.0]nonane, perfluorotrimethylcyclohexane, perfluoroisopropylcyclohexane, perfluoroendotetrahydrodicyclopentadiene, perfluorobicyclo[5.3.0.]decane, perfluorotetramethylcyclohexane, perfluoro-1-methyl-4-isopropylcyclohexane, perfluoro-n-butylcyclohexane, perfluorodimethylbicyclo[3.3.1.]nonane, perfluoro-1-methyl adamantane, perfluoro-1-methyl-4-t-butylcyclohexane, perfluorodecahydroacenaphthlene, perfluorotrimethylbicyclo[3.3.1.]nonane, perfluoro-n-undecane, perfluorotetradecahydrophenanthrene, perfluoro-1,3,5,7-tetramethyladamantane, perfluorododecahydrofluorene, perfluoro-1,3-dimethyl adamantane, perfluoro-n-octylcyclohexane, perfluoro-7-methyl bicyclo[4.3.0.]nonane, perfluoro-p-diisopropylcyclohexane, and perfluoro-m-diisopropylcyclohexane, and perfluorocyclocarbons such as perfluoro (methylcyclohexane), perfluoro (1,3-dimethylcyclohexane), perfluoro (decahydronaphthalene), perfluoro (decahydro-1-methylnaphthalene) and perfluoro (decahydrodimethylnaphthalene), or mixtures thereof, perfluorinated bicyclononane, perfluorinated bicyclooctane, perfluorinated adamantane hydrocarbon, perfluoromethyladamantane and perfluorodimethylbicyclo[3.3.1.]nonane, perfluorodimethyladamantane and perfluorotrimethylbicyclo[3.3.1.]nonane, perfluorotetrahydrodicyclopentadiene and perfluorobicyclo[5.3.0.]decane, perfluorotetrahydrodicyclopentadiene, perfluorinated bicyclononane, perfluorinated bicyclooctane, perfluorinated adamantane hydrocarbon, perfluoromethyladamantane and perfluorotrimethylbicyclo[3.3.1.]nonane, and perfluorotetrahydrodicyclopentadiene and perfluorobicyclo[5.3.0]decane.

In accordance with this description and presently preferred embodiment, it will become apparent that elements other than fluorine may be selected to detect at least one gas in an animal. For example, based upon sensitivity and sufficiency requirements for present NMR techniques, other elements with these properties, specifically, carbon-13, chlorine-35, chlorine-37, deuterium, magnesium-25, nitrogen-14, nitrogen-15, oxygen-17, phosphorous-31, platinum-195, potassium-39, proton, silicon-29, and sodium-23, xenon-129 and other similar elements may be employed.

In another aspect of the present invention, a single gas or gaseous mixture may be detected in an animal. The gases that may be detected by this present invention include biological and foreign gases. Biological gases comprise, but are not limited to blood and tissue gases such as oxygen, carbon dioxide, nitrogen, helium, nitrous oxide and hydrogen, and preferably oxygen, carbon dioxide and nitrogen, and even more preferably, oxygen due to its paramagnetic properties. Foreign gases comprise those gases such as anesthetic or other pharmaceutical gases, or any other gases that may be inhaled or introduced. Further, the detected gas or gases may be homogeneous, or intra- or intermixtures of gases. Thus, the present invention may be used to determine the amount and identity of a homogeneous gas, or an intra- or intermixture of several gases or at least one gas of an intra- or intermixture.

In another aspect of the present invention, due to the advantageous non-invasive, non-ionizing and non-destructive properties of NMR techniques, the novel method of this invention may be employed continuously and in vivo. Further, the magnetic field to be employed with the method of the present invention may be generated by iron-core, resistive air-core, and super conducting air-core magnet designs. Low and high resolution NMR may be employed to detect signals according to the principles of this invention. Whenever possible, however, high-resolution NMR is preferred to detect an element. Upon examination, spectral superimposition or overlapping is undesirable according to the teachings of the present invention and usually will not be observed when, for example, fluorine is being detected. Still further, the method of this invention may be used to determine and monitor a gaseous physiological state in an animal. A basic advantage of such an application provides medical and biological communities with a reliable analytical tool for diagnostic purposes in an animal. Another advantageous embodiment of the present method is that it may be used to detect signals for an element influenced by a gas in at least one region in an animal which corresponds to the distribution of at least one gas in the animal. Thus, therapeutic or sub-therapeutic concentrations of said gases in various regions of an animal may be determined.

In another aspect of the present invention, a detected gas may be uniquely and advantageously imaged into one-, two- or three-dimensional projections reconstructed from chemical shifts, relaxation times such as inversion recovery $T_1$ or spin-echo $T_2$, or spin-spin couplings derived from a detected element influenced by at least one gas in one or more regions in an animal. This objective may be accomplished in accordance with certain principles of this invention by spatially defining detected elements in an animal influenced by at least one gas. For instance, the detected signals in an animal may be for at least one region or a plurality of individual parts along at least one region in an animal. Further, the region may constitute a strip and signals may be detected for a plurality of individual parts, each along at least one strip in an animal. Still further, the region may represent at least one substantially planar slice or a series of parallel planar slices in an animal. If spatial distribution is desired within at least one slice, signals may be detected for at least one strip or a plurality of strips perpendicular to the slice. To further define the spatial distribution of an element influenced by gas in an animal, signals may be detected for at least one part, each along at least one of the strips and at least one of the slices. Still further, the region may also constitute a matrix at least in an area of interest in said animal. The methods to define spatial resolution are well known wherein one or more magnetic gradients may be employed to discriminate areas in which similar elements are located. Any of the teachings to obtain spatial distribution of an element influenced by gas may be employed with the principles of the present invention so long as they do not depart from its spirit. Examples of obtaining spatial distribution are disclosed, for example, in U.S. Pat. Nos. 4,297,637, 4,318,043 and 4,361,807. Once spatial distribution of an element influenced by a gas has been observed, NMR projections may be reconstructed from chemical shift, relaxation times or spin-spin couplings of the element. Such methods may include zeugmatography, NMR tomography, surface coil techniques and chemical microscopy as disclosed in Hall, L. D. and Sukuman, S.: Chemical Microscopy using a High-Resolution NMR Spectrometer. A Combination of Tomography/Spectroscopy Using Either $^1$H or $^{13}$C. 50:161–164 (1982). Of such methods, those taught in Lauterbur et al: Zeugmatographic High Resolution Nuclear Magnetic Resonance Spectroscopy Images of Chemical Inhomogeneity within Macroscropic Objects. J. American Chemical Society. 97(23):6866–6868, Nov. 12, 1975, in U.S. Pat. Nos. 4,319,190 to Brown and 4,361,807 to Burl et al with respect to imaging from chemical shift reconstruction, are preferred and more preferably those taught by Lauterbur and Brown. However, any imaging techniques, such as imaging from projections, FONAR, sensitive point imaging, Fourier imaging, and imaging by selective irradiation, that are compatible with the methods taught by this invention may be employed. As already cited, gases in an animal may further be imaged by such applicable techniques from the relaxation times, e.g., inversion recovery for $T_1$, or spin-echo for $T_2$, and spin-spin couplings observed from the detected element influenced by a gas within an animal.

In a further aspect of the present invention, a radio-frequency reference signal in which chemical shift for an element influenced by a gas in an animal may be established from at least one deuteron or proton. The deuteron may be derived from $D_2O$ incorporated into a perfluorocarbon emulsion or may be substituted onto the perfluorocarbon or derivative thereof. The proton may be derived from $H_2O$ within biological fluids, within a perfluorocarbon aqueous solution or substituted onto the perfluorocarbon or derivative thereof. Still further, the radio-frequency reference signal may be established from an element or moiety of a perfluorocarbon or derivative thereof strategically positioned in the internal phase of an emulsion portion. The unique advantage to this technique is that such an element or moiety would be the least influenced by the surrounding environment providing a more uniform frequency reference signal in which to determine chemical shift therefrom.

EXAMPLE

An uncontaminated 100 cc isotonic and iso-oncotic emulsion is prepared consisting of 10 cc of perfluorocarbons which include perfluorodecalin, perfluoromethyldecalin, perfluoroetherpolymer (Fomblin Y/01), perfluorotrimethylbicyclononane, perfluorotributylamine (FC-47), perfluorotripropylamine, perfluoro-1-3-dimethyladamantane and perfluorotrimethylbicyclo[3.3.1-]nonane (DAWN), perfluoroether (PID), [(CF$_3$)$_2$CFOCF$_2$(CF$_2$)$_2$CF$_2$OCF(CF$_3$)$_2$], perfluoroether (PIID) [(CF$_3$)$_2$CFOCF$_2$(CF$_2$)$_6$CF$_2$OCF(CF$_3$)$_2$],

perfluoropolymer (E4) [CF$_3$CHF(OCF$_2$CF)$_3$OCF$_2$CF$_2$CF$_3$], perfluorohexane, perfluorooctylbromide, 3 grams of hydroxyethyl starch, 2.6 grams of pluronic F-68 (surfactant), 0.2 grams of glucose, 103 mM sodium chloride, 4.5 mM potassium chloride, 2.5 mM calcium chloride, 2.1 mM magnesium chloride, and 25.0 mM sodium bicarbonate, and add a sufficient quantity of sterile water for injection, U.S.P. to make 100 ml.

Typically, a 10% v/v perfluorocarbon emulsion may be prepared with about 3-10% v/v pluronic of choice (surfactant) e.g., about 1-5% XM010. The mixture may be emulsified by either a mechanical process, e.g., Gaulin Homogenizer, or by sonication to produce an emulsion of known characteristics as determined by optical density.

Subsequent to preparation, the mixtures are contaminated by bubbling nitrogen through one typical emulsion until the $PO_2$ is zero mmHg as indicated by a $PO_2$ electrode. Thereafter, oxygen is bubbled through the mixture in a second tube until the $PO_2$ is about 145 mmHg as indicated by the $PO_2$ electrode. In a third tube, oxygen is bubbled through the same mixture until the $PO_2$ is about 700 mmHg as indicated by the $PO_2$ electrode. Of course, the $PO_2$ will be dependent upon, for example, the barometric pressure and other factors at that time of contamination.

Thereafter, the three tubes are subjected to an NMR spectrometer for purposes of detecting known chemical shifts, spin-spin couplings or relaxation times which reflect zero mmHg, 145 mmHg and 700 mmHg of oxygen, respectively.

Once the spectrometer is calibrated, another uncontaminated sample of the same emulsified mixture is introduced intravenously into a mouse wherein NMR spectral characteristics are thereafter recorded by any one of the above cited techniques. Quantitative measurements may then be made by comparing the observed spectrum to detect the average $PO_2$.

In view of the above detailed descriptions and preferred embodiments, the present invention may, of course, be carried out in other specific ways than those herein set forth without departing from the spirit and essential characteristics of the invention. The present embodiments are, therefore, to be considered in all respects as illustrative and not restrictive and all changes coming within the meaning and equivalency range of the appended claims are intended to be embraced therein.

What is claimed is:

1. An NMR composition suitable for introduction into an animal for detecting indirectly a dissolved gas in the animal with an NMR technique, said NMR composition comprising a compound containing a sufficient amount of an element adapted for NMR detection with an NMR technique, the element being influenced by the dissolved gas when said NMR composition is introduced into the animal, and an aqueous liquid mixed with said compound which forms said NMR composition whereby, when said NMR composition is introduced into the animal and the animal is subjected to an NMR spectrometer, a radio-frequency signal derived from the nuclear magnetic resonance of the influenced element can be detected with an NMR technique to generate an NMR parameter which is a function of the dissolved gas.

2. An NMR composition of claim 1 wherein said compound is a perfluorocarbon or derivative thereof and the element is flourine.

3. An NMR composition of claim 2 wherein said NMR composition is an emulsion.

4. An NMR composition of claim 3 wherein said perfluorocarbon or derivative thereof is a perfluorocyclocarbon.

5. An NMR composition of claim 3 wherein said aqueous liquid includes a surfactant.

6. An NMR composition of claim 5 wherein said surfactant is XMO-10.

7. An NMR composition of claim 1 wherein said compound is selected from a group of perfluorocarbon compounds comprising perfluorodecalin, perfluoromethyldecalin, perfluoroetherpolymer (Fomblin Y/01), perfluorotrimethylbicyclononane, perfluorotributylamine (FC-47), perfluorotripropylamine, perfluoro-1-3-dimethyladamantane and perfluorotrimethylbicyclo[3.3.1]nonane (DAWN), perfluoroether (PID) [$(CF_3)_2CFOCF_2(CF_2)_2CF_2OCF(CF_3)_2$], perfluoroether (PIID) [$(CF_3)_2CFOCF_2(CF_2)_6CF_2OCF(CF_3)_2$],

perfluoropolymer (E4) [$CF_3CHF(OCF_2CF)_3OCF_2CF_2CF_3$], perfluorohexane and perfluorooctylbromide.

8. An NMR composition of claim 3 wherein the emulsion is a perfluorocarbon emulsion comprising a perfluorocarbon in an amount on the order of 10% V/V and a surfactant in an amount of about 3-10% V/V.

9. An NMR composition of claim 3 wherein said surfactant is a pluronic surfactant.

10. An NMR composition of claim 1 wherein said compound is a perfluorocyclocarbon.

11. An NMR composition of claim 1 wherein the element is flourine.

* * * * *